United States Patent
Compton et al.

(10) Patent No.: US 6,544,472 B1
(45) Date of Patent: Apr. 8, 2003

(54) METHOD OF MAKING AN ORTHOPAEDIC IMPLANT HAVING A POROUS SURFACE

(75) Inventors: Richard Calvert Compton, Warsaw, IN (US); Clarence Panchison, Warsaw, IN (US); Michael S. Hawley, Warsaw, IN (US); Jay B. Moore, Warsaw, IN (US); William B. Clarke, Winona Lake, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 09/593,794

(22) Filed: Jun. 14, 2000

Related U.S. Application Data

(62) Division of application No. 09/153,507, filed on Sep. 15, 1998, now Pat. No. 6,132,674, which is a continuation-in-part of application No. 09/007,033, filed on Jan. 14, 1998, now Pat. No. 5,926,685, which is a continuation of application No. 08/542,230, filed on Oct. 12, 1995, now Pat. No. 5,734,959.

(51) Int. Cl.[7] ................................................ B22F 7/04
(52) U.S. Cl. ........................ 419/2; 419/9; 427/2.26
(58) Field of Search .................. 264/669; 419/2, 419/9; 427/2, 26

(56) References Cited

U.S. PATENT DOCUMENTS

| | | | |
|---|---|---|---|
| 3,855,638 A | 12/1974 | Pilliar | |
| 3,919,773 A * | 11/1975 | Freeman | 32/10 A |
| 4,612,160 A | 9/1986 | Donlevy et al. | |
| 4,634,720 A * | 1/1987 | Dorman et al. | 521/63 |
| 4,644,942 A | 2/1987 | Sump | |
| 4,661,536 A * | 4/1987 | Dorman et al. | 523/113 |
| 4,713,076 A * | 12/1987 | Draenert | 623/16 |
| 4,834,756 A | 5/1989 | Kenna | |
| 5,061,286 A * | 10/1991 | Lyle | 623/16 |
| 5,080,672 A | 1/1992 | Bellis | |
| 5,098,870 A | 3/1992 | Claar et al. | |
| 5,104,410 A | 4/1992 | Chowdhary | |
| 5,108,964 A * | 4/1992 | Corbett et al. | 501/89 |
| 5,192,324 A | 3/1993 | Kenna | |
| 5,279,994 A * | 1/1994 | Kerkar | 501/94 |
| 5,296,180 A * | 3/1994 | Hayes et al. | 264/44 |
| 5,441,537 A | 8/1995 | Kenna | |
| 5,504,300 A | 4/1996 | Devanathan et al. | |
| 5,705,118 A * | 1/1998 | Hayes et al. | 264/432 |
| 5,732,469 A | 3/1998 | Homamoto et al. | |
| 5,734,959 A | 3/1998 | Krebs et al. | |
| 5,744,532 A * | 4/1998 | Kankawa et al. | 524/440 |
| 5,773,789 A | 6/1998 | Devanathan et al. | |
| 5,776,193 A * | 7/1998 | Kwan et al. | 623/16 |
| 5,861,115 A * | 1/1999 | Hayashi et al. | 264/28 |
| 5,926,685 A | 7/1999 | Krebs et al. | |
| 5,972,284 A * | 10/1999 | Lindsten et al. | 419/2 |
| 5,997,604 A * | 12/1999 | Rafferty et al. | 75/233 |
| 6,187,047 B1 * | 2/2001 | Kwan et al. | 623/16.11 |

* cited by examiner

*Primary Examiner*—Daniel J. Jenkins
(74) *Attorney, Agent, or Firm*—Jacque R. Wilson, Esq.

(57) ABSTRACT

A method of forming an orthopedic implant having a porous surface layer thereon. A mask includes a cut-out configured to receive a portion of the implant therein. The implant is placed within the cut-out and thereby masked. A water soluble binder solution is sprayed onto at least a part of the unmasked portion of the implant using a sprayer, thereby forming a binder layer on the implant. The binder solution includes water, ethanol, gelatin, glycerin, and a colorant. A porous layer including a plurality of metallic particles is contacted with the binder layer. The porous layer is bonded with the surface of the implant with a sintering process.

11 Claims, 5 Drawing Sheets

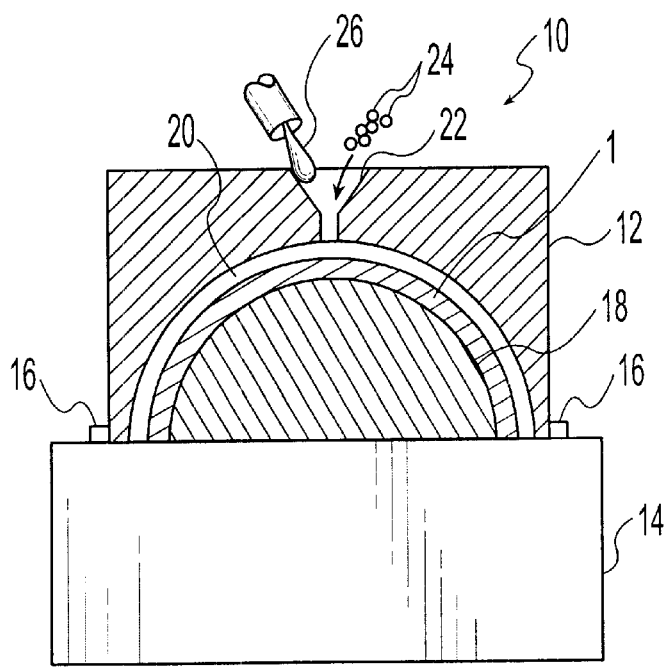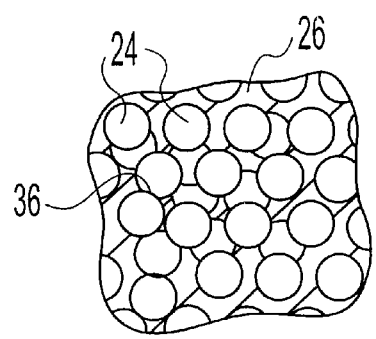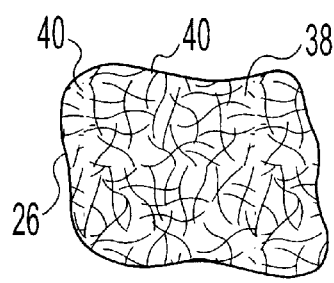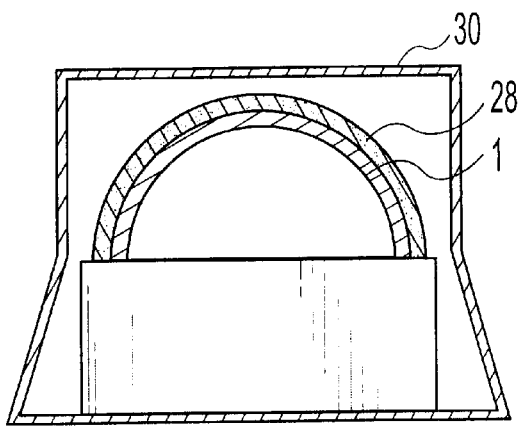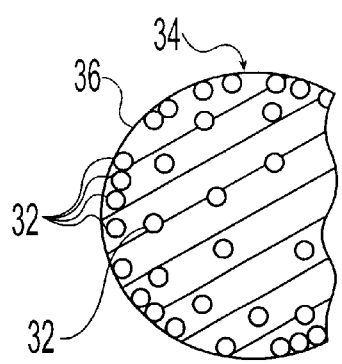
Fig. 1
Fig. 2
Fig. 3
Fig. 4
Fig. 5

METHOD OF MAKING AN ORTHOPAEDIC IMPLANT HAVING A POROUS SURFACE

CROSS REFERENCE TO RELATED APPLICATIONS

This is a divisional of U.S. patent application Ser. No. 09/153,507, filed Sep. 15, 1998, now U.S. Pat. No. 6,132,674, which is a continuation-in-part of U.S. patent application Ser. No. 09/007,033, filed Jan. 14, 1998, now U.S. Pat. No. 5,926,685, which is a continuation of U.S. patent application Ser. No. 08/542,230, filed Oct. 12, 1995, now U.S. Pat. No. 5,734,959.

BACKGROUND OF THE INVENTION

1. Field of the Invention

The present invention relates to orthopaedic implants and, more particularly, to a method of making orthopaedic implants having a porous surface connected thereto by a process utilizing an organic binder compound.

2. Description of the Related Art

Orthopaedic implants of known design may be constructed, e.g., of cobalt-chromium-molybdenum or titanium alloys. Such materials provide suitable physical characteristics of strength, corrosion resistance, wear properties and biocompatability for use in orthopaedic applications.

It is also known to provide an orthopaedic implant with a porous surface at the exterior thereof. The porous surface may be used to promote bone ingrowth and thereby enhance implant fixation within the bone. Alternatively, the porous surface may receive bone cement therein to enhance implant fixation within the bone. Such porous surfaces may be constructed, e.g., of metal beads or metal fibers which are sintered, diffusion bonded, or welded to the implant to form an integral part of the implant.

Presently, fiber metal mesh used to form a porous surface is pressed into a desired shape and maintained under pressure during the sintering process in which some of the fibers are bonded together to form a pad. The process may also be referred to as diffusion bonding. The metal pad is shaped to correspond to its supporting surface and is then positioned in contact with an implant and clamped in place during a sintering process. Alternatively, the fiber metal pad may be gravity sintered, thereby eliminating the use of external clamping forces. A similar process may be employed when making a porous surface using metal beads.

Sintering the porous surface layer to the implant with external pressure is time consuming and expensive for the manufacturer. During sintering, the ramp up and cool down time for the furnace is approximately 14 hours per cycle. If the porous surface layer is being connected, for example, to the interior bone engaging surface of a femoral knee component, it may take 4 complete cycles. The complex geometric interior design of the femoral knee component requires that only one or two pads be attached during one cycle. The typical interior of the femoral knee defines 5 distinct surfaces which require a porous coating. Therefore, to completely bond all of the porous surface layers to the interior of the femoral knee component would require in excess of 56 hours of furnace time. Added to that time is the time required to connect the clamp tooling to the implant for holding the pad in contact with the implant. From the above description, it is clear that providing a porous surface layer on an implant using existing technologies is time consuming and expensive for the manufacturer of orthopaedic implants.

SUMMARY OF THE INVENTION

The present invention provides a method of making an orthopaedic implant having a porous surface by utilizing a water-soluble protein compound such as gelatin to enhance bonding of the porous surface to the implant. Preferably, the gelatin includes an alloying element that is diffused into the metallic particles and lowers the melting temperature of the metallic particles at the interface surfaces by raising the carbon content at the surface of the metal particles. Alternatively, the porous surface layer could be fiber metal mesh impregnated with or otherwise coated by the gelatin. If the porous surface is formed from the plurality of metal wires or fiber metal mesh as it is commonly known, the process includes forming a pad of fiber metal and then impregnating the pad with the gelatin binder. The impregnated pad is then placed in contact with an implant and then gravity sintered.

Regardless of whether the porous layer is formed from a plurality of beads or a layer of fiber metal mesh wire during presintering and sintering, the binder exhibits specific temperature dependent phases. Initially, after the binder is coated over the porous surface layer, or after the impregnated porous layer is applied to the implant, the implant, porous layer, and binder are allowed to dry. Drying causes the binder to become very hard and forms an initial temporary bond between the porous layer and the implant. As the furnace ramps up in temperature, the binder forms a carbon frame-work with the thin porous layer and implant. As the temperature of the furnace continues to increase, some of the carbon becomes defused into the surface of the wires making up the fiber metal mesh. The increased carbon content of the wires decreases the melt temperature of the wires at their surface and causes the wires to fuse or melt bond at contact points with other wires or the implant. Further, if the wires are not in direct contact, the carbon frame-work formed by the binder may assist the melting metal to bridge. Eventually, all of the carbon is defused into the wire and the volatile constituents in the binder are removed leaving the resultant implant substantially free from binder debris. By using the binder and method of the current invention, all of the porous surfaces may be connected to the implant at the same time. As the binder dries and hardens, the binder alone is sufficient to hold the porous surface layers in contact with the implant. Therefore, only one furnace cycle is required to bond a plurality of porous surface layers to the implant. Further, since the binder lowers the melting point of the surface of the wires making up the fiber metal mesh, sintering can be completely accomplished in a shorter sintering cycle and at a lower temperature. Finally, since the binder forms melt bridges between adjacent and the contacting fibers, the bonding within the porous layer is more complete.

In another version of the invention, a plurality of metallic particles are mixed with a water-soluble protein mixture and are spread over the surface of an implant to form a beaded porous surface layer for the implant. For instant, the beads and binder may be poured into a mold to form an outer porous shell of an acetabular cup. The shell is attached to a body of an orthopaedic implant as by sintering or the shell may be sintered separately and placed within an injection mold device to form the outer porous surface of an injection molded polyethylene cup.

In yet another variation of the invention, the binder is used to secure a layer of fine beads to the surface of a fiber metal pad. The fine layer of beads provides a greater contact surface for later sintering the pad to the implant using the binder. This variation could be accomplished by spreading a layer of small beads along the implant surface and then overlying the layer of beads with a layer of fiber mesh. The fiber mesh and beads could then be coated or impregnated with the binder material and then processed according to the teachings set forth above. Alternatively, the bead/fiber metal combination could be presintered together utilizing the binder method of the above invention and then sintered as a unit to the implant, again using the teachings of the subject application. The value of the combination of fiber metal and small beads as described resides in the increased surface area to contact and bond with the implant yet provides the porous fiber metal mat for contact with bone or cement.

While it is believed that the binder alone will be adequate to hold the porous surface layer against the implant, there may be instances or areas on the implant when it may be advantageous to spot weld the pad to the implant to provide initial fixation prior to sintering.

In all variations of the invention, it is important the binder be formed from a protein compound such as gelatin. Gelatin is especially attractive as a binder agent due to its ease of use in a manufacturing environment. The gelatin binder is easy to apply as it does not require any special handling equipment, and it is non-toxic and otherwise safe to handle. Furthermore, if the gelatin is applied incorrectly, it can be washed off with warm water without any damage to the implant or porous surface.

The invention comprises, in another form thereof, a method of forming an orthopaedic implant having a porous surface layer. An orthopaedic implant has a surface configured to support the porous surface layer. A mask includes a cut-out configured to receive a portion of the implant therein. The implant is placed within the cut-out and thereby masked. A water soluble binder solution is sprayed onto at least a part of the unmasked portion of the implant using a sprayer, thereby forming a binder layer on the implant. A porous layer including a plurality of metallic particles is contacted with the binder layer. The porous layer is bonded with the surface of the implant with a sintering process.

The invention comprises, in yet another form thereof, a mask for covering a portion of an orthopaedic implant during manufacture. At least two blocks of material have adjoining surfaces. At least one of the blocks has a cut-out in the corresponding adjoining surface. The cut-outs are configured to receive the portion of the implant therein. At least one fastening device fastens the at least two blocks together.

The invention comprises, in still another form thereof, a binder solution for application to an orthopaedic implant to bind a metallic porous layer with at least a portion of the implant. The binder solution is a mixture including gelatin and water. Preferably, glycerine is added as a plasticizer. Also preferably, alcohol is added to facilitate a uniform mist to be applied to form a uniform coating of binder. More preferably, a colorant is added to facilitate visually gauging binder coating thickness.

An advantage of the present invention is that external forces (and associated machinery) are not required to hold the porous layer to the implant during the sintering operation.

Another advantage of the present invention is that external forces (and associated machinery) are not required to hold the shell defining the porous surface during the sintering operation.

Another advantage is that the shell can be moved from one location to another prior to the sintering operation without damaging the physical integrity thereof.

Yet another advantage is that the binder may include an alloying material which is diffused into the metallic particles, thereby lowering the melting point at the interface surfaces of the metallic particles which is less than the melting point of the material from which the metallic particles are initially constructed.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 1 is a side, sectional view of an embodiment of a mold assembly used in the method of the present invention illustrating a shell of metal beads and binder being poured into the mold over a metal acetabular cup;

FIG. 2 is a side, sectional view of the shell of FIG. 1 disposed within an embodiment of a diagrammatically illustrated furnace;

FIG. 3 is a fragmentary view of a shell molded with the mold in FIG. 1, including beads and a binder, FIG. 4 is a fragmentary view of a shell molded with the mold in FIG. 1, including metal fibers and a binder;

FIG. 5 is a cross-sectional diagrammatical view of a bead shown in FIG. 3, illustrating a high carbon content of alloying material at the surface of the bead after a sintering process, illustrated in FIG. 2, is complete;

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 6:
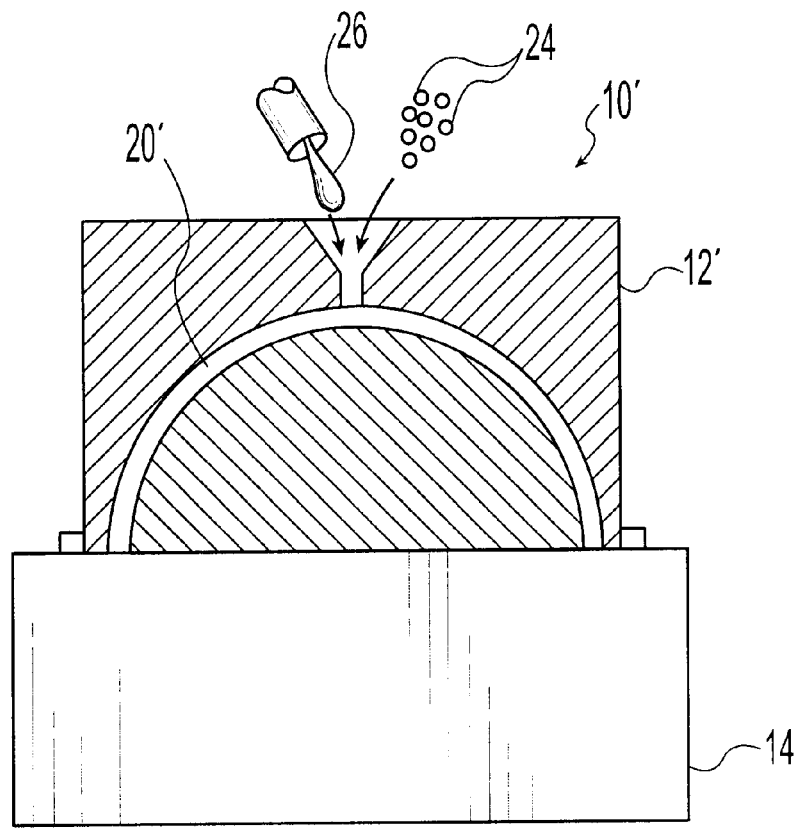
FIG. 6 is a side, sectional view of an embodiment of a mold assembly used in the method of the present invention.

Referring now to the drawings, and particularly to FIG. 1, there is shown an embodiment of a mold assembly 10 which can be utilized to form a porous surface for use in an orthopaedic implant. Mold assembly 10 generally includes a first mold half 12 and a second mold half 14. Second mold half 14 includes a flange 16 for positioning first mold half 12 relative thereto. Further, second mold half 14 includes a contoured surface 18 which is either integral with or separably associated with second mold half 14. For example, contoured surface 18 may be in the form of a prosthetic implant which is separately associated with second mold half 14.

As illustrated, second mold half 14 is configured to accommodate and otherwise support a metal acetabular cup 1. It should be understood that while an acetabular cup is illustrated, this should not be considered a limitation on the invention. For example, the invention could apply equally to the fixation of a porous layer to the exterior surface of a femoral hip stem implant, or femoral knee joint component with the molds altered respectively. As another example, contoured surface 18 may be in the form of a prosthetic implant which is separately associated with second mold half 14.

First mold half 12, with acetabular cup 1 supported thereon, and contoured surface 18 of second mold half 14 define a mold cavity 20 therebetween. Mold cavity 20 is in communication with an inlet 22 which is sized and configured for receiving metallic particles 24 therein. Metallic particles 24 may be in the form of metal beads. Inlet 22 is also adapted to receive a binder therein, such as a water soluble protein mixture 26. In the embodiment shown in FIG. 1, protein mixture 26 is in the form of gelatin 26 having an alloying material (to be discussed hereinafter) therein. Gelatin 26 is preferably suspended in water at a concentration between 0.10% to 50% by weight. Glycerin may also be added to the gelatin mixture as a plasticizer. In one embodiment, the gelatin mixture consists essentially of 10 ml. of water, 0.75 grams gelatin, and 0 02 to 0 05 grams glycerin.

During use, metallic particles 24 and gelatin 26 may be mixed together and introduced into mold cavity 20, such that the mixture substantially and entirely fills mold cavity 20 about the outer surface of acetabular cup 1. Mold cavity 20 is configured to form a shell about the cup having a desired shape with the mixture of metallic particles 24 and gelatin 26. After the mixture fills the mold cavity, gelatin 26 is allowed to set-up or harden within mold cavity 20. Alternatively, the mixture, mold and implant may be frozen to allow the mold halves to be separated and the implant removed. In either instance, the implant with the gelatin and bead mixture adhered thereto is allowed to dry for a period of time. Drying causes the gelatin to become very hard.

After drying, implant 1 with shell 28 adhering thereto is placed within a furnace 30 shown in simplified form in FIG. 2. Furnace 30 provides the dual functionality of both converting the gelatin mixture substantially to carbon, and bonding metallic particles 24 together via sintering. More particularly, after shell 28 is placed within furnace 30, the air within furnace 30 is evacuated using a pump or other suitable mechanism (not shown) down to a pressure of $1 \times 10^{-5}$ TORR pressure. Furnace 30 is thereafter backfilled by pumping an inert gas such as high purity argon therein to pressure zero (0) PSIG. Subsequently, furnace 30 is again evacuated by pumping the high purity argon within furnace 30 down to a pressure of $1 \times 10^{-5}$ TORR. This evacuating and backfilling process is repeated two additional times and furnace 30 is thereafter backfilled with high purity argon to a partial pressure of at least 100 micrometers. Reactive gases such as nitrogen, hydrogen and mixture of nitrogen and hydrogen gas can also be used in the process. The temperature within furnace 30 is then increased at a rate of 5 to 25° F. per minute, preferably 10 to 15° F. per minute, to a predetermined temperature of 800 to 1,500° F., preferably 1200 to 1400° F., more preferably 1300° F., and held at this temperature for 10 to 15 minutes or until the temperature reaches equilibrium. Furnace 30 is then heated again at a rat of 5 to 25° F. per minute, preferably 10 to 15° F. per minute, to a predetermined temperature of 2200to 2300° F., and held at this temperature for 10 to 15 minutes or until the temperature reaches equilibrium. Furnace 30 is finally heated again at a rate of 1 to 15° F. per minute, preferably 5° F. per minute, to a sintering temperature of 2300 to 2425° F., preferably 2,365° F. and held at this temperature for a time period of between 15 minutes to 8 hours which is effective for carrying out a sintering process which provides an implant having a suitable bead bond strength for a particular application. It is anticipated that the preferred final hold time will be approximately 1 to 4 hours, preferably approximately 4 hours.

In the embodiment shown in FIGS. 1 and 2, metallic particles 24 and gelatin 26 are mixed prior to delivery within mold cavity 20. However, it is to be understood that metallic particles 24 can be introduced into mold cavity 20, and gelatin 26 can thereafter be injected into mold cavity 20

When shell 28 is disposed in furnace 30 and the temperature therein is increased at the predetermined rate as described above, at a temperature around 1300° F. the gelatin mixture within shell 28 is converted essentially into residual carbon which then covers metallic particles 24. The carbon defines an alloying material which is diffused into metallic particles 24 from which metallic particles 34 are made (FIG. 5). Further, as the furnace temperature ramps up, all volatile constituents in the binder are removed leaving only the carbon. For example, FIG. 5 illustrates a fragmentary, sectional view of a metal bead after the diffusion of carbon 32 therein from the binder as described above to form metal bead 34. Since the gelatin contacts only the periphery of the bead, carbon 32 may be disposed at a higher concentration about the periphery 36 of metal bead 34, as shown (FIG. 5). The carbon illustrated deeper within the bead represents carbon already present in the bead. Carbon 32 within alloyed metal bead 34 results in a lower melting point at the interface surface (e.g. periphery) of alloyed metal bead 34. That is, the eutectic composition of alloyed metal bead 34 having carbon 32 therein results in an interface surface 36 having an eutectic melting point which is less than the melting point of the Co-Cr-Mo alloy from which alloyed metal bead 34 is initially constructed. The sintering process takes place at a temperature which is less than the eutectic melting point of alloyed bead 34, which in turn is less than the melting point of the Co-Cr-Mo alloy from which alloyed metal bead 34 is constructed.

In the embodiment shown in FIG. 5, the alloying material within alloyed metal bead 34 is in the form of carbon 32, as described above However, it is also possible that the alloying material can be in the form of silicon, ferrosilicon, F-75 alloy, and/or iron. Such alloying material is typically in the form of a powder which is suspended within gelating 26 (FIG. 1).

Referring now to FIG. 3, an enlarged, fragmentary view of shell 28 shown in FIG. 2 is illustrated prior to carbonization of gelatin 26. Metallic particles 24 are in the form of metal beads 24 which are held together using gelatin 26. Metal beads 24 may contact adjacent metal beads 24 along respective interface surfaces 36 (FIGS. 3 and 5)

Referring now to FIG. 4, an enlarged, fragmentary view of an alternate embodiment of a shell is shown. A metal layer is partially illustrated formed from metallic metal mesh as is well known in the industry. The metal mesh is formed from a plurality of metal fibers 38 which are in contact with each other at respective interface surfaces 40. Metal fibers 38 are held in place prior to sintering using gelatin 26 (FIG. 1) which has been allowed to set-up.

Figure 7:
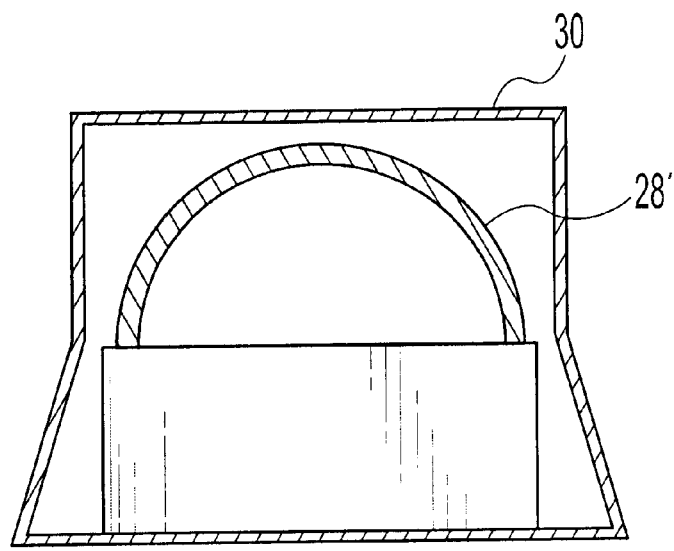
FIG. 7 is a side, sectional view of a shell molded with the mold of FIG. 6, and disposed within an embodiment of a diagrammatically illustrated furnace.

In the embodiments described above, metallic particles 24 and binder 26 are introduced within mold cavity 20 of mold assembly 10. However, it is also to be understood that a mixture of metallic particles 24 and binder 26 can be manually applied to an orthopaedic implant surface, such as a contoured surface 18 shown in FIG. 1. Further, it is also possible to use a mixture of metallic particles 24 and binder 26 within a compression molding and/or injection molding machine to form a shell 28'. As illustrated in FIGS. 6 and 7, a shell 28' is formed using a mold 10' having an upper mold portion 12 and a lower mold portion 14. A mold cavity 20' is formed between the upper and lower mold portions and may be filled with metal beads 24 and binder 26. After molding, the shell 28' is dried and then sintered in over 30 (FIG. 7) to form a rigid porous shell. The rigid porous shell 28' may then be placed in an injection mold machine to form the porous backing for a molded acetabular cup.

Figure 8A:
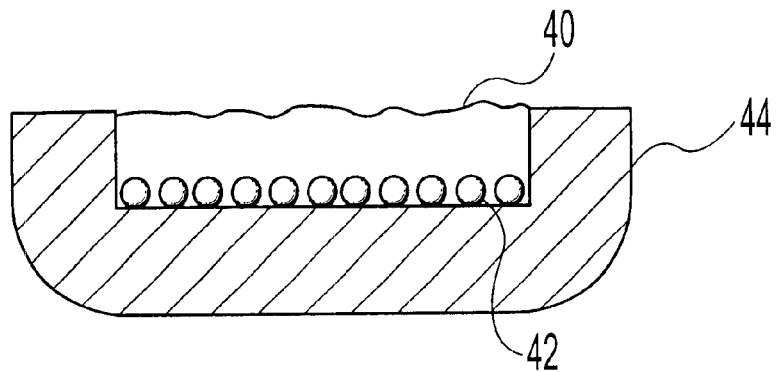
FIG. 8A is a side sectional view of an implant having a porous surface layer formed consistent with the invention and including a layer of metal beads between the implant and a layer of fiber metal mesh.
Figure 8B:
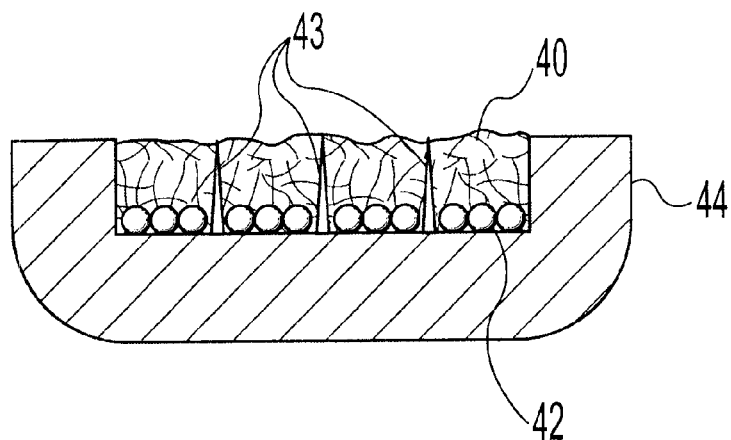
FIG. 8B is a side sectional view of an implant having a porous surface layer formed consistent with the invention and including a plurality of spot welds to hold the porous layer in position prior to sintering.

A further example of the usefulness of the binder method of this invention is illustrated in FIG. 8A wherein a fiber metal mesh pad 40 is connected to an implant 44 via a layer of small beads 42. In use, the beads are layered on the implant and the fiber mesh is supported by the layer of beads The beads and mesh are coated or impregnated with the binder. The binder and implant are processed in a manner consistent with the above method. During sintering, the small beads are bonded to the fiber mesh and to the implant. Alternatively, several spot welds 43 (preferably formed by a laser welder) may be used (FIG. 8B) to fix the metal pad 40 and beads 42 in place on the implant 44 prior to sintering. The advantage of such a construction would be two fold. First, the bead would present the greater surface area and thereby bond better with the implant as compared to fiber metal. Second, the fiber metal is believed to form a better area for the ingrowth of bone as compared to the beads.

Figure 9:
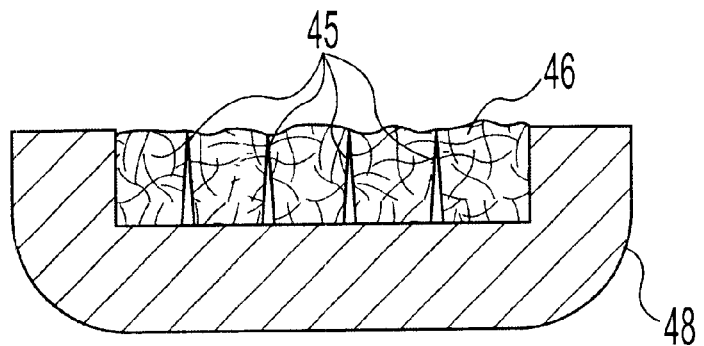
FIG. 9 is a side sectional view of an implant having a porous surface layer formed consistent with the invention and including a plurality of spot welds to hold the porous layer in position.

While it is believed that the binder will, when dry, adequately hold a layer of fiber metal mesh to the implant during sintering, FIG. 9 illustrates a potential variation of the method of the invention In the embodiment of FIG. 9, after the fiber metal is positioned on the implant, several spot welds 45 are made to fix the metal mesh 46 to the implant 48 prior to sintering. Either before or after the spot welding, the metal mesh is impregnated with the binder material consistent with the above description.

It has been found that if cobalt-chromium-molybdenum metallic beads 24 are used which have an initial concentration of 0.24 to 0.26% carbon, the final carbon content within metal beads 34 (FIGS. 3 and 5) using the process of the present invention is approximately 0.31%. It is therefore possible to vary the final carbon content within metal beads 34 by varying the initial carbon concentration within metal beads 34 and the concentration of carbon within gelatin 26.

Figure 10:
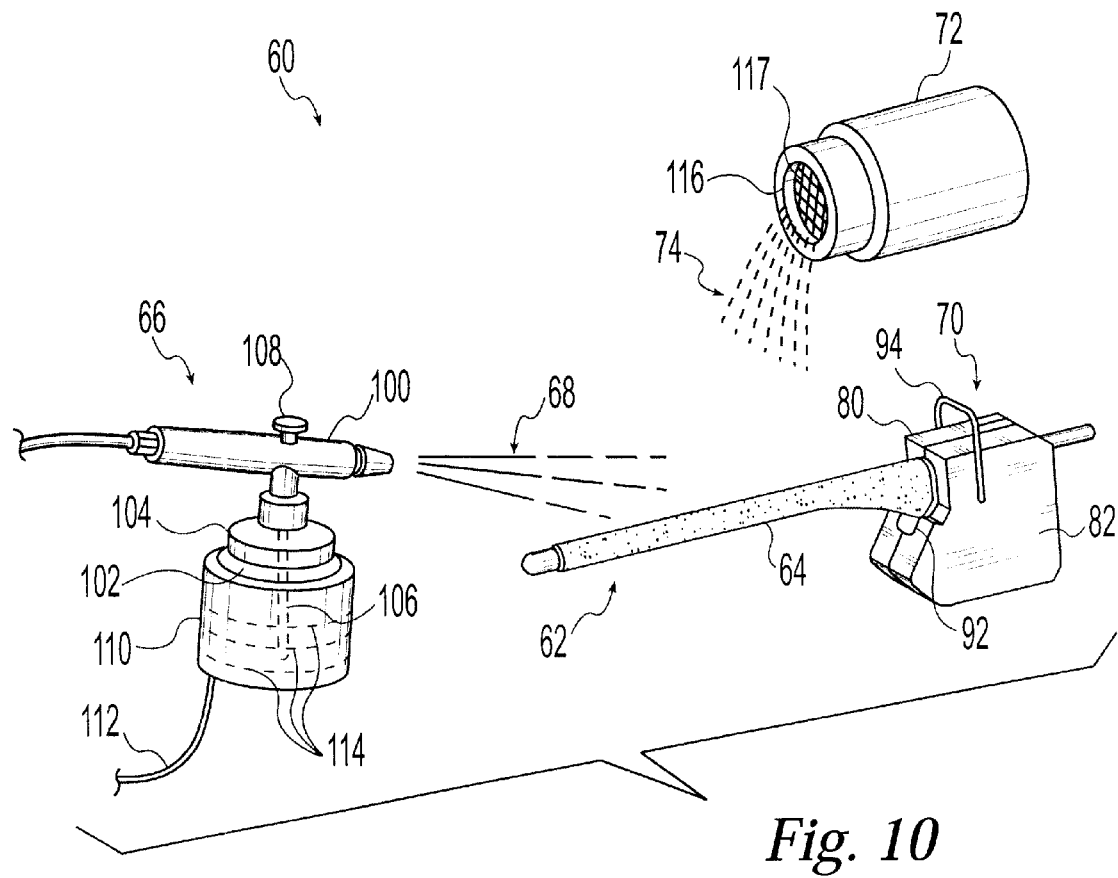
FIG. 10 is a perspective view of an embodiment of a system of the present invention for forming an orthopaedic implant with a porous surface layer.
Figure 11:
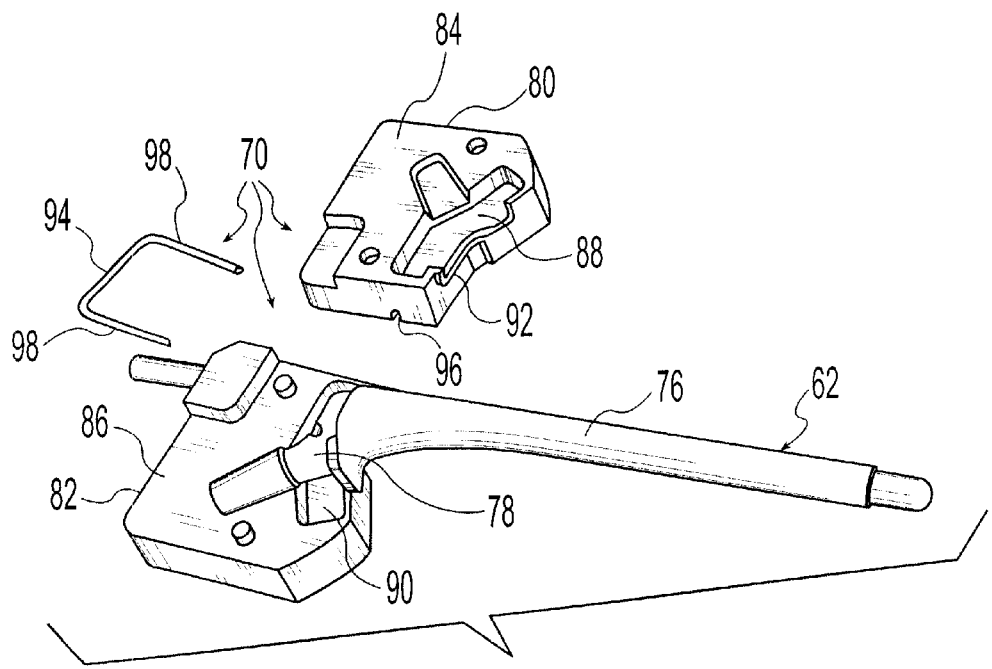
FIG. 11 is an exploded, prospective view of the mask and proximal hip implant shown in FIG. 10.

Referring now to FIGS. 10 and 11, there is shown another embodiment of a system 60 of the present invention for forming an orthopaedic implant 62 having a porous surface layer 64. System 60 also generally includes a sprayer 66 for spraying a water soluble binder solution 68 onto at least a portion of implant 62; a mask 70 for masking a portion of implant 62 from the applied binder solution 68; and a container 72 for applying a plurality of metallic particles 74 onto implant 62 to form porous surface layer 64.

Implant 62, which in the embodiment shown is a femoral hip implant, may be generally formed using known methods prior to application of porous surface layer 64 thereon. Implant 62 has a surface 76 (FIG. 11) which is configured to support porous surface layer 64. In the embodiment shown, surface 76 corresponds to a stem portion of implant 62 which is received within a prepared opening in a proximal femur.

Mask 70 covers a portion 78 of implant 62 which is not intended to be covered with porous surface layer 64 during manufacture. Mask 70 includes two blocks 80 and 82 of plastic material with respective adjoining edges 84 and 86. Each block 80 and 82 includes a respective cutout 88 and 90 in and extending from a corresponding adjoining edge 84 and 86. Cutouts 88 and 90 are configured to receive portion 78 of implant 62 which is not intended to be covered with porous surface layer 64. When connected together, cutouts 88 and 90 of blocks 80 and 82 define an exit opening 92 from which implant 62 extends. Exit opening 92 is configured to lie closely adjacent to implant 62 when implant 62 is within mask 70, such that binder solution 68 does not impinge upon portion 78 of implant 62 which is not intended to be covered by binder solution 68 In the embodiment shown, the remaining portions of cut-outs 88 and 90 adjacent to exit opening 92 also lie closely adjacent to portion 78 of implant 62 disposed within mask 70. However, the remaining portions of cutouts 88 and 90, except for the portions defining exit opening 92, need not necessarily lie closely adjacent to portion 78 of implant 62. Thus, mask 70 is configured to provide the primary functionality of preventing binder solution 68 from impinging upon portion 78 which is not intended to be covered by binder solution 68 and/or porous surface layer 64

When implant 62 is disposed within mask 70, blocks 80 and 82 are fastened together using a suitable fastening device In the embodiment shown, a generally U-shaped member 94 is used to bias blocks 80 and 82 together along adjoining edges 84 and 86. More particularly, each of blocks 80 and 82 include a slot 96 in an exterior surface thereof which is generally opposite from a corresponding adjoining edge 84 or 86. U-shaped member 94 includes two legs 98 which are spaced apart a predetermined distance which is just slightly smaller than the distance between slots 96 when blocks 80 and 82 are assembled together. Each leg 98 is received within a corresponding slot 97 and holds blocks 80 and 82 together using a compressive clamping action. It is also possible to use a different type of fastening device other than a U-shaped member 94. For example, blocks 80 and 82 may be fastened together using screws, bolts, springs, etc.

Sprayer 66, in the embodiment shown, is a conventional compressed air paint sprayer, such as a hobby-type air brush. Sprayer 66 includes a gun 100 which is connected with a source of compressed air (not shown), and a receptacle 102 which attaches with gun 100 and receives binder solution 68 therein. Receptacle 102 includes a screw top 104 which allows substantially sealed interconnection with gun 100. A dip tube 106 extending from gun 100 into receptacle 102 allows binder solution to be drawn from within receptacle 102 for use with gun 100. A plunger 108 on top of gun 100 may be manually depressed to open a valve within gun 100 to drawn binder solution 68 into gun 100

An insulated holder 110 is configured to receive receptacle 102 therein. Holder 110 preferably lies closely adjacent to receptacle 102, and frictionally engages receptacle 102 when coupled therewith. Holder 110 includes at least one heater therein which receives electrical power through an electrical conductor 112 connected with a source of electrical power (not shown). In the embodiment shown, insulated holder 110 includes a single electrical resistance wire 114 which is placed in a suitable pattern within holder 110 to provide a sufficient power density to heat binder solution 68 within receptacle 102 to a desired temperature. For example, electrical resistance wire 114 may be placed in a serpentine or helical pattern within insulated holder 110 to provide a suitable power density to each of receptacle 102 and binder solution 68. Preferably, the power density associated with electrical resistance wire 114 is sufficient to heat binder solution 68 within receptacle 102 to a temperature of between approximately 40° C. and 100° C., and more preferably to a temperature of between approximately 50° C. and 75° C. The purpose of heating the binder solution 68 is to cause it to flow more freely so that it may be more readily sprayed.

Binder solution 68 is in the form of a water soluble binder solution with fluid properties allowing binder solution 68 to be sprayed on to implant 62 using sprayer 66. Binder solution 68 is a mixture including gelatin and water. Preferably, glycerine is added as a plasticizer. Also preferably, alcohol is added to facilitate a uniform mist to be applied to form a uniform coating of binder. More preferably a colorant is added to facilitate visually gauging binder coating thickness. To prepare the binder, a mixture of ethyl alcohol and water is made. Other alcohols could be used but it has been found that ethyl alcohol offers the least toxicity and the best mixing with water and gelatin. The mixture can range from 80% to 20% ethyl alcohol by volume. The preferred mixture is, 40% to 60% ethyl alcohol, more preferably approximately 50% ethyl alcohol by volume. To each 100 ml of this mixture is added 0.5 to 15 grams, preferably 5.0 to 7.0 grams of gelatin To this mixture is added 0.1 to 5.0 grams, preferably 1.0 to 2.0 grams, of glycerin. To this mixture is added 0.1 to 5.0 ml, preferably 2.0 to 4.0 ml of colorant. An exemplary binder consists essentially of 50 ml of water; 50 ml of ethanol; 5.80 grams of gelatin; 1.50 grams of glycerin; and 2.9 ml green food coloring. The gelatin and glycerin are each organic materials including carbon therein. The carbon defines an alloying material which may be defused into the metallic particles 74, as will be described hereinafter. The content of carbon within binder solution 68 may be adjusted by adjusting the amount of gelatin and/or glycerin within binder solution 68. The ethanol is preferably denatured with isopropanol and acts as a thinner to adjust the viscosity of binder solution 68 as well as the carbon content within binder solution 68. Moreover, the ethanol is allowed to evaporate when binder solution 68 is sprayed onto implant 62, thereby both cooling as well as accelerating the setting of binder solution 68. The evaporating ethanol increases the evaporation of water from the solution further speeding drying. In the embodiment shown, the particular type of ethanol used is obtained from VWR, catalog number 1B 15720. Moreover, in the embodiment shown, the particular type of gelatin which is used is Knox brand (TM) gelatin.

The colorant allows a user to determine a thickness of the binder layer formed by binder solution 68 on implant 62 by matching a shade of the colorant in the binder solution with a predetermined shade of the colorant corresponding to a desired binder layer thickness. The present inventors have recognized that the human eye detects shades of the color green better than other colors Accordingly, the colorant which is used in binder solution 68 is a green colorant, preferably McCormick's brand (TM) green food coloring. If the binder layer formed from binder solution 68 which is sprayed onto implant 62 is too thin, the shade of green will be too light and if the binder layer is too thick the shade of green will be to dark. If the observed shade of green is to light, a user simply sprays more binder solution 68 onto implant 62. On the other hand, if the shade of green is to dark, the user may simply wash off binder solution 68 from implant 62 and repeat the spraying process until a desired shade of green is obtained.

Container 72 includes metallic particles 74 therein. Metallic particles 74 may be in the form of metal fibers or metal beads, and preferably are in the form of metal beads in the embodiment shown. Container 74 includes a shaker opening 116 having a mesh 117 with a predetermined mesh size which allows metal beads 74 to pass therethrough when container 72 is inverted and shaken. Metal beads 74 may thus be sprinkled onto binder solution 68 covering surface 76 of implant 62. Metal beads 74 which contact binder solution 68 will be held in place, while metal beads 74 which do not contact binder solution 68 are allowed to fall to a collection and recycling container (not shown) disposed under implant 62 during the manufacturing process.

Figure 12:
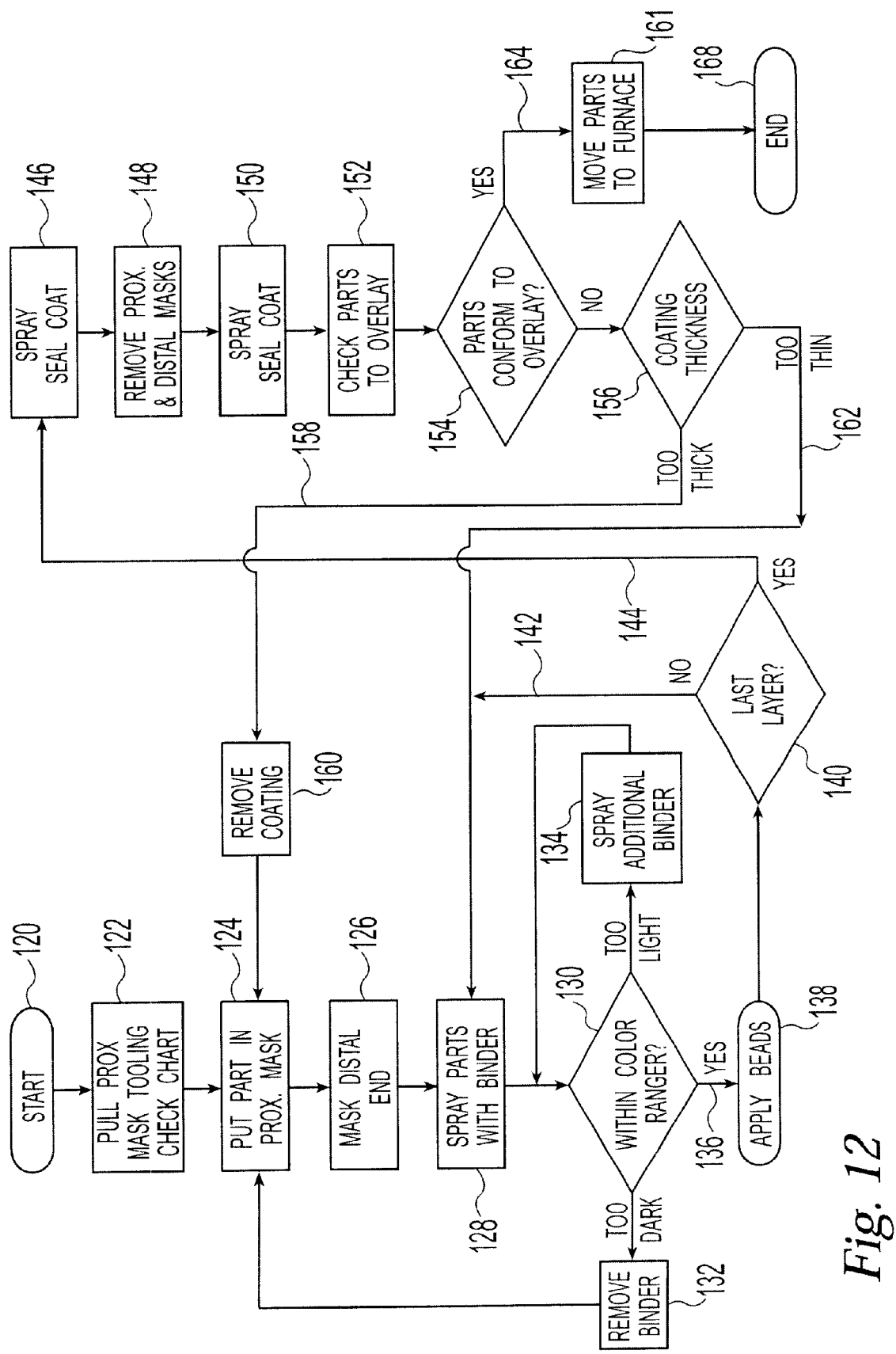
FIG. 12 is a flow chart of an embodiment of a method for forming the proximal hip implant with a porous surface layer of FIG. 10.

Referring now to FIG. 12, an embodiment of a method of manufacturing an implant 62 with a porous surface layer 64 thereon will be described in more detail. At the start 120 of the manufacturing process, the particular type and size of implant which is desired to be covered with a porous layer 64 is checked and correlated with a corresponding size and shape mask (block 122). For purposes of illustration, the implant is assumed to be proximal femoral implant 62 shown in FIGS. 10 and 11 Implant 62 is then placed in mask 70 such that only a portion of implant 62 is exposed (block 124) The distal end of implant 62 is then masked by simply wrapping tape around a predetermined length at the distal end thereof (block 126). Mask 70, containing implant 62, may then be held in one hand by a user, while sprayer 66 is operated with the other hand to apply binder solution 68 to implant 62, thereby forming a binder layer on implant 62 (block 128). The shade of the green colorant which is in the binder layer on implant 62 is then visually inspected to determine whether the thickness of the binder layer is correct (decision block 130). If the green color is too dark, then the binder layer is too thick and is removed by simply washing the water soluble binder from implant 62 (block 132). On the other hand, if the green color is too light, the thickness of the binder layer is to thin and an additional coating of binder solution 68 is sprayed onto implant 62 using sprayer 66 (block 134). If the green color is within a prescribed range, then the thickness of the binder solution and resulting binder layer is satisfactory (line 136). Metallic particles in the form of metallic beads are then applied to the binder layer by sprinkling the metallic beads onto the binder layer using container 72 (block 138). After the first layer of metallic beads 74 are applied to implant 62, the process of spraying another binder layer onto implant 62 and applying another layer of metallic beads 74 is repeated until a total of three layers of beads have been applied (decision block 140 and line 142). After the third layer of metallic beads have been applied to implant 62 (line 144), a seal coating is sprayed over the final layer of metallic beads (block 146). Implant 62, including porous surface layer 64 thereon, is then removed from mask 70, and the tape is removed from the distal end of implant 62 (block 148). An additional seal coating is then applied to implant 62, including porous surface layer 64 (block 150) Implant 62 is then checked with an overlay pattern (block 152) to verify that the total thickness of the metallic bead layers falls within an acceptable range. If implant 62 and porous surface layers 64 do not conform to the overlay pattern in a manner which indicates that the total thickness of the bead layers is too thick, then the binder solution and metallic beads are washed off of implant 62 and the process repeats at block 124 (as indicated by decision block 156, line 158 and block 160). On the other hand, if implant 62 and porous surface layer 64 do not conform to the overlay pattern in a manner which indicates that the total thickness of the metallic beads 74 is too thin, then an additional binder layer and coating of metallic beads 74 are applied to the implant 62 (as indicated by decision block 156 and line 162). If the implant 62 and porous surface layer 64 are determined to conform to the overlay pattern, then implant 62 with porous surface layer 64 is placed into a furnace to bond metallic bead 74 to implant 62 using a sintering process (line 164 and block 166), thus completing the manufacturing process of implant 62 (block 168).

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of forming a orthopedic implant having a porous surface layer, said method comprising the steps of providing an orthopedic implant; spraying a water soluble binder solution on the implant, wherein the binder solution comprises: water and a water-soluble protein gelatin, said gelatin comprising an alloying element selected from the group consisting of carbon, silicon, ferrosilicon, iron, and F-75 alloy; and contacting a porous layer having a plurality of metallic particles with said binder solution; and bonding said porous layer with said implant.

2. The method of claim 1, wherein the binder solution further comprises alcohol.

3. The method of claim 2, wherein the alcohol is ethanol.

4. The method of claim 3, wherein the ethanol is 20% to 80% by volume relative to the water.

5. The method of claim 4, wherein the ethanol is 50% by volume relative to the water.

6. The method of claim 1, wherein the binder solution further comprises: alcohol; glycerin; and colorant.

7. The method of claim 6, wherein for 100 ml of alcohol and water combined, the binder solution includes:

alcohol in the range of 20% to 80% by volume of the alcohol and water;

gelatin in the range of 0.5 to 15 grams;

glycerin in the range of 0.1 to 5 grams; and colorant in the range of 0.1 to 5 milliliters.

8. The method of claim 7, wherein for 100 ml of alcohol and water combined, the binder solution includes:

alcohol in the range of 40% to 60% by volume of the alcohol and water;

gelatin in the range of 5.0 to 7.0 grams;

glycerin in the range of 1.0 to 2.0 grams; and colorant in the range of 2.0 to 4.0 milliliters.

9. The method of claim 8, wherein said binder solution consists essentially of:

50 ml±0.2 ml of said water;

50 ml±0.2 ml of said ethanol;

5.80 grams±0.02 grams of said gelatin;

1.50 grams±0.02 grams of said glycerin; and 2.9 ml±0.1 ml of said colorant.

10. The method of claim 9, wherein said ethanol is denatured with isopropanol.

11. The method of claim 10, wherein said colorant is green food coloring.

\* \* \* \* \*